US00PP11736P2

(12) United States Plant Patent

Zary

(10) Patent No.: US PP11,736 P2
(45) Date of Patent: Jan. 9, 2001

(54) FLORIBUNDA ROSE PLANT NAMED 'JACPAN'

(75) Inventor: Kieth W. Zary, Thousand Oaks, CA (US)

(73) Assignee: Bear Creek Gardens, Inc., Medford, OR (US)

( * ) Notice: Under 35 U.S.C. 154(b), the term of this patent shall be extended for 0 days.

(21) Appl. No.: 09/040,217

(22) Filed: Mar. 17, 1998

(51) Int. Cl.[7] ..... A01H 5/00
(52) U.S. Cl. ..... Plt./150
(58) Field of Search ..... Plt./141, 142, 149, Plt./150

*Primary Examiner*—Howard J. Locker
(74) *Attorney, Agent, or Firm*—Klarquist, Sparkman, Campbell, Leigh & Whinston, LLP

(57) ABSTRACT

Floribunda rose plant having flowers of a unique color, and having thick, leathery petals; good clustering ability; and good cut flower production.

1 Drawing Sheet

The present invention relates to a new and distinct variety of rose plant of the floribunda class which was originated by me by crossing the variety 'JACpray', (not patented), with the variety 'JACanne', U.S. Plant Pat. No. 8,634.

The primary objective of this breeding was to produce a new rose variety having the strong clustering ability and well formed flowers of the female parent combined with the thick petals and strong stems of the male parent. The objective was substantially achieved, along with other desirable improvements, as evidenced by the following unique combination of characteristics that are outstanding in the new variety and that distinguish it from its parents, as well as from all other varieties of which I am aware:

1. Thick, leathery petals;
2. Unique flower color;
3. Good clustering ability; and
4. Good cut flower production.

'JACpan' is a clustering floribunda bred for cut flower production. It produces 170–180 stems/m$^2$ in a greenhouse under Somis, Calif. conditions.

Asexual reproduction of this new variety by budding, as performed at Wasco, Calif. shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'JACpray', not patented.

*Pollen parent.*—'JACanne', U.S. Plant Pat. No. 8,634.

Classification:

*Botanical.*—Rosa hybrida.

*Commercial.*—Floribunda.

FLOWER

Observations made from specimens grown in a greenhouse environment at Somis, Calif. from January 1997 to February 1998.

Blooming habit: Continuous

Bud:

*Size.*—About ¾ inches long when the petals start to unfurl.

*Form.*—Long, pointed ovoid.

*Color.*—When sepals first divide, bud color is Red Group 45D. When half blown, the upper sides of the petals are Red Group 44B, and the lower sides of the petals are Red Group 45D.

*Sepals.*—Color: Green Group 138B. Surface texture: Covered in fine hairs. There are three lightly appendaged sepals. There are two unappendaged sepals with hairy edges.

*Receptacles.*—Color: Yellow-Green Group 146B. Shape: Funnel. Size: Small (about ¼"×⅛"). Surface: Smooth.

*Penduncle.*—Length: Short (averaging about 1¾"). Surface: Smooth. Color: Yellow Green Group 146C. Strength: Stiff, erect.

Bloom:

*Size.*—Small. Average open size is about 2½".

*Borne.*—In flat clusters of five to eight flowers.

*Stems.*—Long (average about 22–24"), strong.

*Form.*—When first open: High centered. Permanence: Flattens, outer petal edges curl slightly.

*Petalage.*—Number of petals under normal conditions: 30.

*Color:*—The upper sides of the petals are Red Group 44B. The reverse sides of the petals are Red Group 45D. The base of each petal has a small (3/16"×3/16"), Yellow Group 2D half moon at the point of attachment. The major color on the upper sides is Red Group 44B.

*Variegations.*—Occasional whitish streak on the guard petals.

*Discoloration.*—At end of the first day: No change. At the end of the third day: No change. By day 7 or 8 there is a change (in the vase) to Red Group 43C on the upper petal surface and to Red Group 51A on the lower surface. By day 10 the petals drop.

*Fragrance.*—None.

Petals:

*Texture.*—Thick, leathery.

*Shape.*—Round to deltoid.

*Form.*—Tips slightly recurved.

*Arrangement.*—Imbricated. Petaloids in the center: Few, small.

*Persistance.*—Petals drop off cleanly before drying.

*Lastingness:*—On the plant: Long (7–8 days). As a cut flower: Long (10 days).

Reproductive Parts:

*Anthers.*—Size: Medium. Quantity: Many. Color: Yellow. Arrangement: Regular around styles.

*Filaments.*—Color: Greenish white.

*Pollen.*—Color: Lemon yellow.

*Styles.*—Color: Greenish white.

*Stigmas:*—Color: Greenish white.

Plant:

*Form.*—Bush.

*Growth.*—Vigorous; upright; branching. At maturity, in the greenhouse after one year, height is 4½ to 5 feet, width is 3½ to 4 feet.

Foliage: Number of leaflets on normal mid-stem leaves: Five or seven.

*Size.*—Medium (6" long ×4½" wide).

*Quantity.*—Abundant.

*Color.*—New foliage: Upper and lower sides: Greyed-Red Group 178A. Old foliage: Upper side: Green Group 139A. Lower side: green Group 138B.

Leaflets:

*Shape.*—Oval.

*Texture.*—Leathery, glossy.

*Edge.*—Serrated.

*Serration.*—Single, small.

*Petiole rachis.*—Color: Green Group 139A.

*Petiole underside.*—Smooth, with an occasional prickle.

*Stipules.*—Long (⅞"), serrated.

*Disease resistance.*—Resistant to mildew under normal growing conditions at Somis, Calif.

Wood

*New wood.*—Color: Greyed-Purple Group 183C. Bark: Smooth.

*Old wood.*—Color: Green Group 137C. Bark: Rough.

Prickles:

*Quantity.*—On main canes from base: Ordinary. On laterals from main canes: Ordinary.

*Form.*—Medium (⅜"), hooked downward.

*Color when young.*—Greyed-Purple Group 185A.

Small Prickles:

*Quantity.*—On main stalks: None. On laterals: None.

I claim:

1. A new and distinct variety of rose plant of the floribunda class, as herein shown and described, characterized particularly by flowers of a unique color, and having thick, leathery petals; good clustering ability; and good cut flower production.

* * * * *

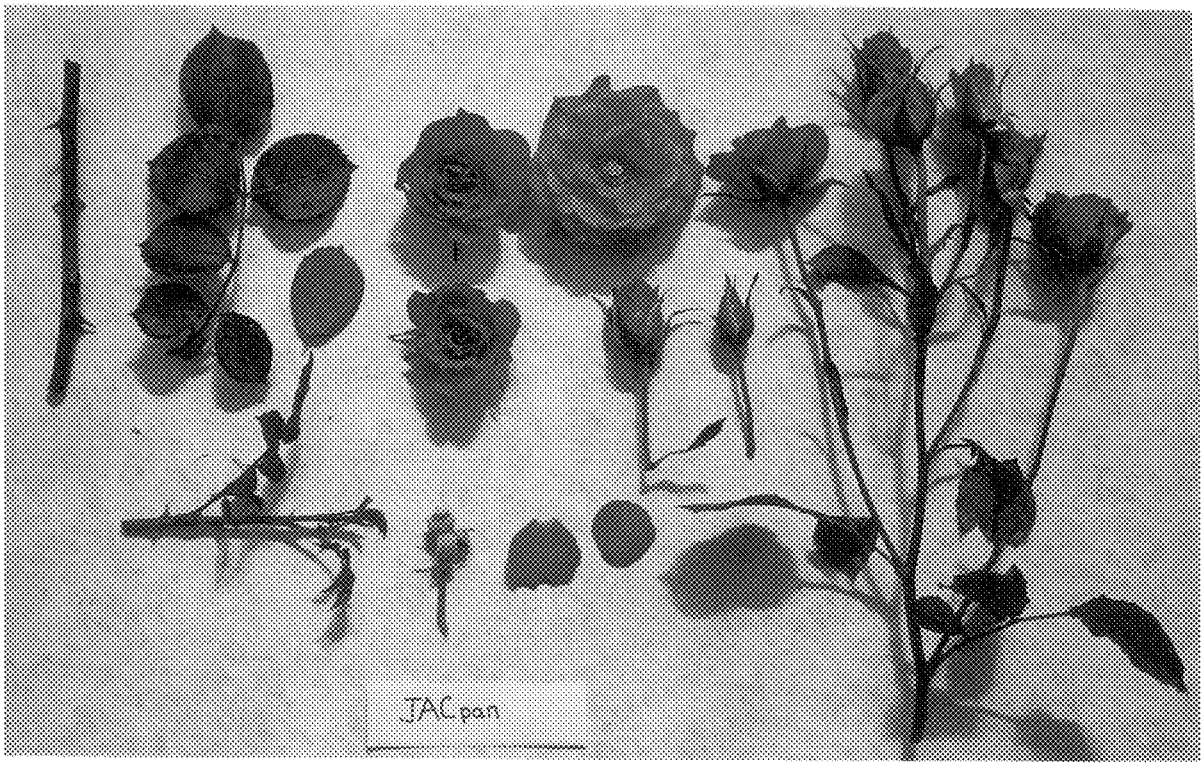
JACpan